United States Patent
Tybinkowski et al.

(10) Patent No.: US 6,776,527 B1
(45) Date of Patent: Aug. 17, 2004

(54) PATIENT TABLE DOCKING SYSTEM AND METHOD FOR TOMOGRAPHY SCANNERS

(75) Inventors: Andrew P. Tybinkowski, Boxford, MA (US); Robert F. Riemer, Andover, MA (US); Robert M. Williams, Wilmington, MA (US); Eric Bailey, Hampton, NH (US)

(73) Assignee: Analogic Corporation, Peabody, MA (US)

( * ) Notice: Subject to any disclaimer, the term of this patent is extended or adjusted under 35 U.S.C. 154(b) by 69 days.

(21) Appl. No.: 10/198,691

(22) Filed: Jul. 16, 2002

Related U.S. Application Data
(60) Provisional application No. 60/305,736, filed on Jul. 16, 2001.

(51) Int. Cl.[7] .................................................. A61B 6/04
(52) U.S. Cl. ........................................ 378/209; 378/195
(58) Field of Search ................................ 378/208, 209, 378/195, 117, 4; 5/621, 600, 601, 84.1; 600/415

(56) References Cited

U.S. PATENT DOCUMENTS

| | | | |
|---|---|---|---|
| 4,131,802 A | | 12/1978 | Braden et al. |
| 4,567,894 A | * | 2/1986 | Bergman .................... 600/415 |
| 4,727,328 A | | 2/1988 | Carper et al. |
| RE36,415 E | | 11/1999 | McKenna |
| 6,345,193 B2 | * | 2/2002 | Dutto et al. ................ 600/415 |
| 6,346,706 B1 | * | 2/2002 | Rogers et al. ......... 250/363.04 |
| 6,389,623 B1 | * | 5/2002 | Flynn et al. ................... 5/611 |
| 6,459,923 B1 | * | 10/2002 | Plewes et al. .............. 600/411 |

* cited by examiner

Primary Examiner—Edward J. Glick
Assistant Examiner—Hoon Song
(74) Attorney, Agent, or Firm—McDermott Will & Emery LLP

(57) ABSTRACT

A table docking system including a table having a base supported by at least two wheels, and at least one docking station having a plate, and a guide wall positioned and oriented with respect to the plate such that a pathway for the wheels of the patient table is defined between the guide wall and the plate. Another docking system constructed in accordance with the present inventions includes a table having a base defining a groove, and at least one docking station having a plate and at least one vertical projection extending from the plate and sized for receipt within the groove of the base of the patient table. Systems of the present inventions can be used, for example, to quickly and easily move a patient table between multiple tomography scanners.

20 Claims, 2 Drawing Sheets

PATIENT TABLE DOCKING SYSTEM AND METHOD FOR TOMOGRAPHY SCANNERS

CROSS-REFERENCE TO RELATED APPLICATION

The present application claims priority to co-pending provisional U.S. patent application Ser. No. 60/305,736, which was filed on Jul. 16, 2001, is assigned to the assignee of the present application, and is incorporated herein by reference.

FIELD OF THE INVENTIONS

The present inventions relates generally to tomography systems and, more specifically, to a patient table movable between multiple tomography systems. Even more specifically, the present inventions are directed to a patient table docking system and method for allowing a single patient table to be used between multiple tomography systems.

BACKGROUND OF THE INVENTIONS

CT scanners have been used for over twenty-five years to create images of cross-sectional slices of subjects, such as human patients, and are particularly used as a medical diagnostic aid. A CT scanner can produce a 3-dimensional anatomic image of a patient's body.

An annular gantry normally supports many of the components of a CT scanner and includes an outer ring secured to a stand and an inner ring mounted for rotation within the outer ring. During a scanning procedure, a patient table is positioned through the center of the gantry and the inner ring is rotated about the table. The components supported by the gantry can include an x-ray tube for providing the x-ray beam, one or more high voltage power supplies, balancing weights, a data acquisition module, and a bank of detectors diametrically opposed from the x-ray source. At least some of these components are secured in the inner ring for rotation therewith.

PET scanning is a more recently developed procedure that uses positron emitting radioactive isotopes to show function or metabolism, rather than anatomy as in CT scanning techniques. A PET scanner is made up of special radiation detectors called scintillators which are arranged in a ring configuration within an annular gantry. Basically, each detector has an associated partner detector oppositely located on the ring. This setup allows for the sensing and measurement of positrons emitted by radioactive isotopes injected into a patient. The measurements are processed through nuclear counting equipment and computers to produce 3-dimensional images that allow quantitation of the physiochemical process in the patient's body. PET scanners are used to diagnose and monitor cancer, in addition to diseases of the heart, brain and lungs.

Recently, the results of different types of scanning procedures, e.g., PET and CT scans (and MRI and x-ray procedures), have been combined, or superimposed, to take advantage of the particular benefits of each procedure. Accordingly, a patient is first scanned using a first procedure, then scanned using a second procedure, and the results of both scans are combined using specialized software and computing systems.

In order to obtain tomographic images of a patient with either scanner, it is necessary that the patient be located exactly at a predetermined position inside the opening of an annular scan gantry of the apparatus. For this reason, such scanners have been provided with a patient handling couch or table which is moveable vertically to be in line with an axis of the scan gantry, and moveable axially in and out of the scan gantry.

Patient tables and systems and methods for correctly positioning or docking the tables against scanning machines exist. For example, U.S. Pat. Nos. 4,131,802; 4,567,894; 4,727,328; and Re. 36,415 show patient tables and systems and methods for docking the tables against scanning machines.

What is still desired, however, are new and improved systems and methods that allow scanners, such as a CT scanner and a PET scanner, to be combined into a single system. What is specifically desired is a new and improved patient support couch or table that is movable between two or more scanning machines. What is further desired are systems and methods for easily, quickly and correctly positioning a movable patient table with respect to a scanning machine, to accommodate the ability to move the table among multiple scanning machines.

SUMMARY OF THE INVENTIONS

The present inventions accordingly provides systems and methods for allowing a single patient table to be moved between at least two scanning machines, and easily, quickly and correctly positioned with respect to the gantry of each scanning machine.

According to one aspect of the present inventions, the table docking system includes a table having a base supported by at least two wheels, and at least one docking station having a plate, and a guide wall positioned and oriented with respect to the plate such that a pathway for the wheels of the patient table is defined between the guide wall and the plate. The docking station can be positioned with respect to a gantry of a scanning machine such that the patient table is correctly positioned with respect to the scanning machine when the wheels of the table are received in the pathway of the docking station.

According to another aspect of the present inventions, the table docking system includes a table having a base defining a groove, and at least one docking station having a plate and at least one vertical projection extending from the plate and sized for receipt within the groove of the base of the patient table. The docking station can be positioned with respect to a gantry of a scanning machine such that the patient table is correctly positioned with respect to the scanning machine when the vertical projection of the docking station is received in the groove of the table.

The foregoing and other features and advantages of the present inventions will become more readily apparent from the following detailed description of the disclosure, as illustrated in the accompanying drawing.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
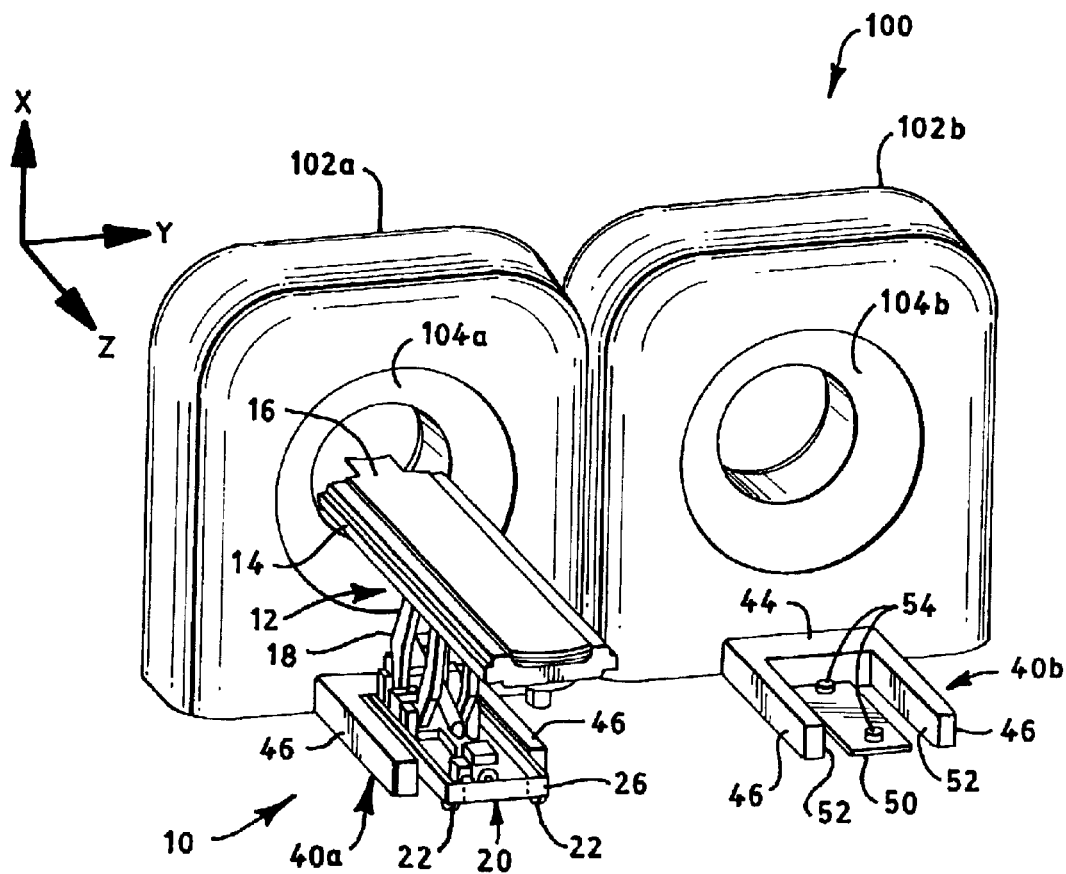
FIG. 1 is a top and end perspective view of an exemplary embodiment of a patient table docking system and method constructed in accordance with the present inventions, with identical docking stations of the system shown positioned respectively against first and second tomography scanners, and a patient table of the system shown received in one of the docking station such that it is properly aligned with the first tomography scanner.

Referring first to FIG. 1, a tomography scanner system 100 is shown with an exemplary embodiment of a patient table docking system 10 constructed in accordance with the present inventions. Among other features and advantages, the docking system 10 of the present inventions allows a single patient table 12 to be moved between at least two scanning machines 102a, 102b of the tomography scanner system 100, and easily, quickly and correctly positioned with respect to a gantry 104a, 104b of each scanning machine 102a, 102b.

In the exemplary embodiment of FIG. 1, the tomography scanner system 100 includes two side-by-side gantries 104a, 104b of scanning machines 102a, 102b, such as a CT scanner and a PET scanner. The system 100, however, can be provided with more than two gantries or other types of medical diagnostic machines. As is known to one skilled in the art of x-ray tomography scanning, each of the scanner machines 102a, 102b includes an annular gantry 104a, 104b containing therein components for conducting a tomography scan on a patient positioned within the gantry of the machine.

For example, in a computed tomography (CT) scanner, the annular gantry 104 contains an x-ray source that projects a beam of x-rays toward a detector array on an opposite side of the gantry 104. During a scanning procedure, the annular gantry 104 and the components mounted thereon rotate about a center of rotation, which is parallel and aligned with a z-axis of a Cartesian coordinate system shown in FIG. 1. The x-ray beam is collimated to lie within in an x-y plane of the Cartesian coordinate system and pass through a patient lying on the patient table 12 within an opening of the gantry 104. The detector array within the gantry 104 senses the projected x-rays that pass through the patient and produces electrical signals that represent the intensity of the attenuation of the x-ray beam passing through the patient.

Although not shown, rotation of the gantries 104a, 104b and the operation of the components contained within the gantries are governed by at least one control mechanism of the scanner system 100. The control mechanism, for example, can include an x-ray controller that provides power and timing signals to the x-ray source within the CT scanner gantry and a gantry motor controller that controls the rotational speed and position of the gantry. A data acquisition system (DAS) of the control mechanism samples analog data from the detector array of the gantry 102 and converts the data to digital signals for subsequent processing. An image reconstructor receives the sampled and digitized x-ray data from the DAS and performs high speed image reconstruction, which is applied as an input to a computer which stores the image in a mass storage device.

The computer of the control mechanism of the scanner system 100 in turn receives commands and scanning parameters from an operator via an input device, such as a keyboard, and a video display allows the operator to observe the reconstructed image and other data from computer. The operator supplied commands and parameters are used by the computer to provide control signals and information to the DAS, the x-ray controller and the gantry motor controller.

The computer of the scanner system 100 can also be used to control operation of the patient table 12 to correctly position a patient through the central openings in the gantries 104a, 104b. In particular, after the patient table 12 is correctly positioned with respect to one of the gantries 104a, 104b, as shown in FIG. 1, the patient table 12 is operated to lift a patient vertically (parallel with the x-axis) to a desired position with respect to the rotation axis (z-axis) of the gantry before beginning a scanning procedure. During the scanning procedure, the patient table 12 is then operated to move a patient horizontally through the annular gantry in a direction parallel with the rotation axis (z-axis) of the gantry.

Figure 3:
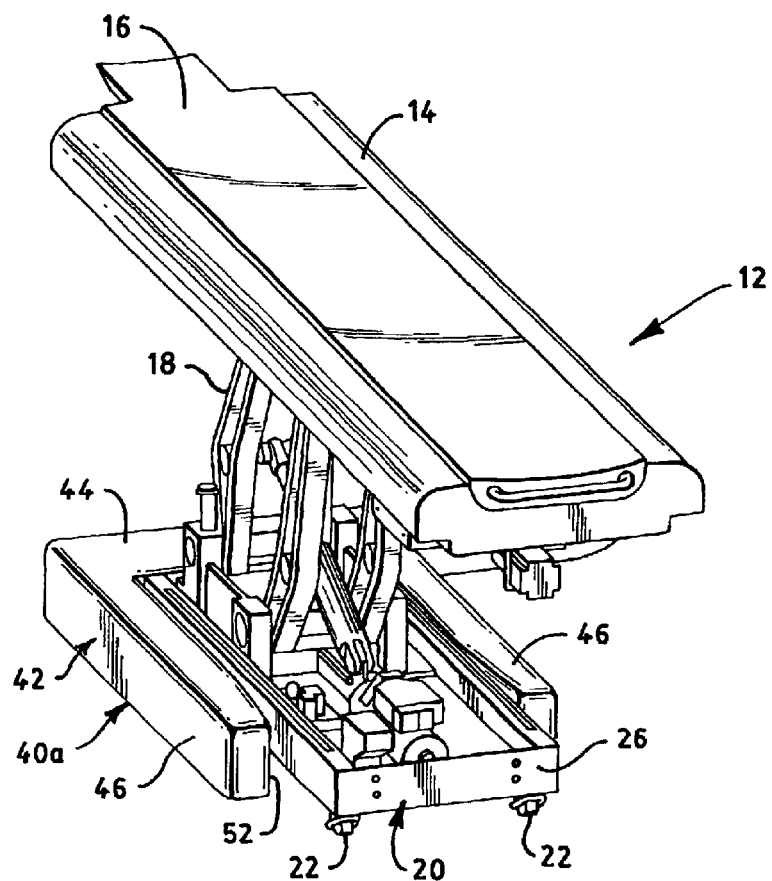
FIG. 3 is an enlarged top and end perspective view of the patient table and one of the identical docking stations of FIG. 1.

Referring also to FIG. 3, the patient table 12 includes an elongated table assembly 14 and an elongated pallet 16 positioned on the table assembly. As shown, the table 12 is positioned with respect to the gantry 104a such that the elongated pallet 16 extends parallel with the rotation axis (z-axis) of the gantry 104a. The elongated pallet 16 is shaped and sized for a patient to lie thereon in alignment with the rotation axis (z-axis) of the gantry 104a. The pallet 16 is movable on the table assembly 14 to extend a patient horizontally through the annular gantry 104a in a direction parallel with the rotation axis (z-axis) of the gantry. An exemplary embodiment of a table assembly, a pallet and a horizontal drive mechanism for moving the pallet on the table assembly is disclosed in co-pending U.S. patent application Ser. No. 10/161,910, filed Jun. 3, 2002, which is assigned to the assignee of the present application and incorporated herein by reference. However, the present invention is not meant to be limited by the specific table assembly, pallet or horizontal drive mechanism employed in the patient table 12.

The patient table 12 also includes a lifting apparatus 18 supporting the table assembly 14 and the pallet 16. The lifting apparatus 18 is used to lift the table assembly 14, the pallet 16 and a patient supported thereon, vertically (parallel with the x-axis) to a desired position with respect to the rotation axis (z-axis) of the gantry 104a before beginning a scanning procedure. An exemplary embodiment of a lifting apparatus is disclosed in co-pending U.S. patent application Ser. No. 10/161,184, filed Jun. 3, 2002, which is assigned to the assignee of the present application and incorporated herein by reference. However, the present invention is not meant to be limited by the specific lifting apparatus employed in the patient table 12.

The patient table 12 includes a base 20 supporting the lifting apparatus 18 and having wheels 22 for allowing the table to be moved among the different scanners 102. In the exemplary embodiment of FIGS. 1 and 3, the base 20 is generally rectangular and elongated and includes first and second opposite ends 24, 26 and two opposite sides 28, 30. The wheels, which preferably comprise swiveling castors 22, are positioned at each corner of the base 20 such that the base includes a total of four wheels 22.

The docking system 10 of the present invention also includes at least one docking station 40a, 40b for receiving the patient table 12 and automatically positioning the patient table 12 in a correct position with respect to the scanner machines 102a, 102b. In the exemplary embodiment of FIG. 1, the system 10 includes two docking stations 40a, 40b, one positioned in a predetermined manner with respect to each of the gantries 104a, 104b, respectively, so that the position of the patient table 12 received in the station 40a, 40b is known relative to the gantries 104a, 104b.

Figure 2:
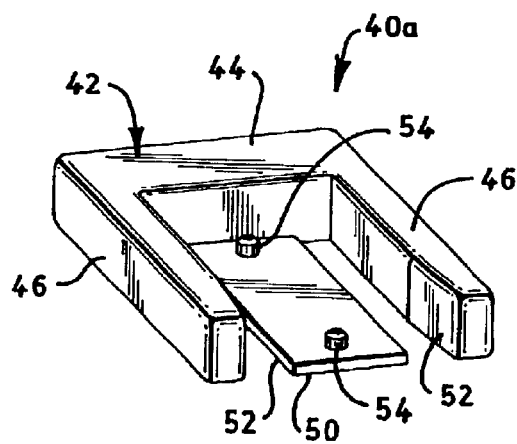
FIG. 2 is an enlarged top and end perspective view of one of the identical docking stations of FIG. 1.

As also shown in FIG. 2, the docking stations 40a, 40b are identical and each station 40a, 40b includes a generally U-shaped wall 42 including an end wall 44 for abutting the gantry 104a, 104b, and outer guide walls 46 extending generally perpendicular from the end wall 44 for receiving, guiding and positioning the sides 28, 30 and the first end 24 of the base 20 of the patient table 12. Each station 40a, 40b also includes a plate 50 positioned within the wall 42. The base 20 of the table 12 has a ground clearance greater that the plate 50 such that the base 20 can move over the plate 50. Each plate 50 is sized and shaped such that pathways 52 are defined between the plate 50 and the guide walls 46 for receiving, guiding and positioning the wheels 22 of the base 20 of the patient table 12. In addition, each station 40a, 40b includes at least one vertical projection 54 extending upwardly from the plate 50.

Figure 4:
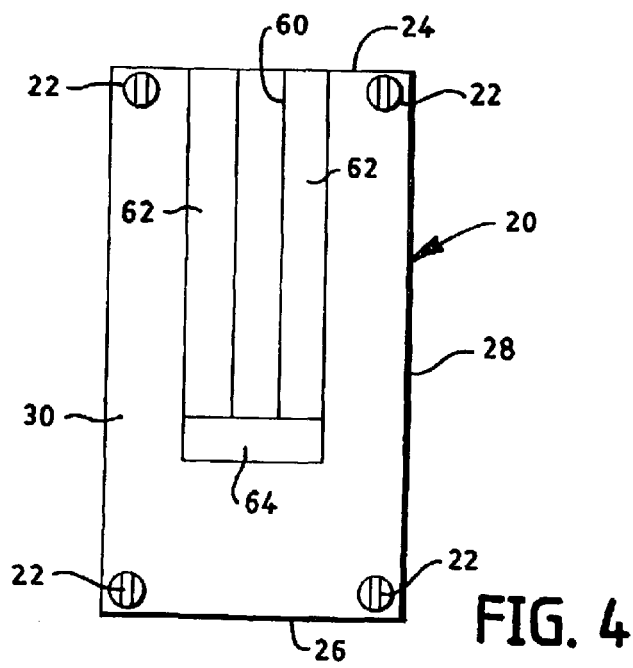
FIG. 4 is a bottom plan view of a base of the patient table of FIG. 1.

Referring also to FIG. 4, the base 20 of the patient table defines a groove 60 on an underside, or lower surface, of the base 20 for receiving the at least one vertical projection 54 of the docking station 40a, 40b. The groove 60 extends from the first end 24 of the base 20 towards the second end 26. In the exemplary embodiment of FIG. 4, the groove 60 is defined by two spaced-apart, parallel, longitudinally extending members 62 secure to the lower surface of the base 20 and that extend from the first end 24 of the base to a lateral member 64 also secured on the lower surface. Although not show, the base 20 can also be provided with means for releasably latching onto the vertical projection 54 of the docking station 40a, 40b. In the exemplary embodiment of FIGS. 1 and 2, the at least one vertical projection of the docking stations 40a, 40b comprise two spaced-apart, cylindrical vertical projections 54.

The present inventions therefore provides a new and improved patient table 12 that is movable between two or more scanning machines 102a, 102b, and docking stations 40a, 40b for easily, quickly and correctly positioning the movable patient table 12 with respect to gantries 104a, 104b of each scanning machine.

While the patient table 12 and the docking stations 40a, 40b of the present inventions are described and shown as being used with an x-ray tomography machine, they can also be used in other applications.

It should be understood that the embodiments of the present inventions described herein are merely exemplary and that a person skilled in the art may make variations and modifications to the embodiments described without departing from the spirit and scope of the present inventions. All such equivalent variations and modifications are intended to be included within the scope of these inventions as defined by the appended claims.

What is claimed is:

1. A table docking system comprising:
   a table including a base supported by at least two side by side wheels; and
   at least one docking station which is positioned with respect to an annular gantry of a tomography scanner system so that the table will be aligned in a repeatable manner with a center of rotation of the gantry when the table is received in the docking station, the docking station including,
   a plate receivable on a surface supporting the gantry of the tomography scanner system, and
   a guide wall receivable on the surface supporting the gantry spaced from the plate and positioned and oriented with respect to the plate such that a pathway for one of the side by side wheels of the patient table is defined between the guide wall and the plate.

2. A table docking system according to claim 1, wherein the base table is elongated and includes opposing first and second ends, and the docking station includes an end wall for receiving the first end of the base.

3. A table docking system according to claim 2, wherein the docking station includes two of the guide walls and the guide walls are spaced-apart and parallel and extend substantially perpendicular from the end wall of the docking station, and wherein the plate is positioned between the two guide walls, and wherein two of the pathways for the wheels of the patient table are defined between the guide walls and the plate.

4. A table docking system according to claim 3, wherein a distance between the guide walls is substantially equal to a distance between opposite sides of the base of the table.

5. A table docking system according to claim 1, wherein the docking station further includes at least one vertical projection extending from the plate and sized for receipt within a groove of the base of the patient table.

6. A table docking system according to claim 5, wherein the groove is defined on a lower surface of the base.

7. A table docking system according to claim 6, wherein the base of the table is elongated and includes opposing first and second ends, and the groove extends from the first end of the base.

8. A table docking system according to claim 1, wherein the vertical projection of the docking station is cylindrical.

9. A table docking system according to claim 1, wherein the vertical projection of the docking station comprises two spaced-apart vertical projections.

10. A tomography scanner system including the table docking system of claim 1, and further comprising an annular gantry rotatable about a horizontal center of rotation and containing therein an x-ray source for projecting a beam of x-rays across the center of rotation to a detector array on an opposite side of the gantry, wherein the docking station is positioned with respect to the gantry such that the patient table can be aligned with the center of rotation of the gantry when received in the docking station.

11. A table docking system comprising:

a table including a base having a groove; and at least one docking station which is positioned with respect to an annular gantry of a tomography scanner system so that the table will be aligned in a repeatable manner with a center of rotation of the gantry when the table is received in the docking station, the docking station including, a plate receivable on a surface supporting the gantry of the tomography scanner system, and at least one vertical projection extending from the plate and sized for receipt within the groove of the base of the patient table when the base is positioned over the plate.

12. A table docking system according to claim 11, wherein the groove is defined on a lower surface of the base.

13. A table docking system according to claim 12, wherein the base of the table is elongated and includes opposing first and second ends, and the groove extends from the first end of the base.

14. A table docking system according to claim 11, wherein the vertical projection of the docking station is cylindrical.

15. A table docking system according to claim 11, wherein the vertical projection of the docking station comprises two spaced-apart vertical projections.

16. A table docking system according to claim 11, further comprising a guide wall receivable on a surface supporting the gantry of the tomography scanner system, and positioned and oriented with respect to the plate such that a pathway for wheels supporting the base of the patient table is defined between the guide wall and the plate.

17. A table docking system according to claim 16, wherein the base of the table is elongated and includes opposing first and second ends, and the docking station includes an end wall for receiving the first end of the base.

18. A table docking system according to claim 17, wherein the docking station includes two guide walls and the guide walls are spaced-apart and parallel and extend substantially perpendicular from the end wall of the docking station, and wherein the plate is positioned between the two guide walls, and wherein two of the pathways for the wheels of the patient table are defined between the guide walls and the plate.

19. A table docking system according to claim 18, wherein a distance between the guide walls is substantially equal to a distance between opposite sides of the base of the table.

20. A tomography scanner system including the table docking system of claim 11, and further comprising an annular gantry rotatable about a horizontal center of rotation and containing therein an x-ray source for projecting a beam of x-rays across the center of rotation to a detector array on an opposite side of the gantry, wherein the docking station is positioned with respect to the gantry such that the patient table can be aligned with the center of rotation of the gantry when received in the docking station.

* * * * *